US00PP32040P2

(12) United States Plant Patent
Hansen

(10) Patent No.: US PP32,040 P2
(45) Date of Patent: Aug. 4, 2020

(54) ***HOSTA* PLANT NAMED 'DANCING WITH DRAGONS'**

(50) Latin Name: ***Hosta* hybrid (Tratt.)**
Varietal Denomination: Dancing with Dragons

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,619

(22) Filed: Nov. 8, 2019

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
CPC ... A01H 5/12; A01H 5/02; A01H 5/00; A01H 6/12; A01H 6/56
See application file for complete search history.

*Primary Examiner* — June Hwu

(57) ABSTRACT

A new and distinct *Hosta* plant named 'Dancing with Dragons' of arching, ovate, strongly glaucous, blue-green leaves having a near white underside and wavy margins. The blue-green leaf coloration remains until near the end of the growing season. The flowers with white tepals having light lavender centers are tightly congested in verticils and individually on scapes above the foliage. 'Dancing with Dragons' has excellent compact mounded habit and is useful in the landscape, in containers, as a specimen or en masse.

2 Drawing Sheets

Botanical classification: *Hosta* hybrid (Tratt.).
Variety denomination: 'Dancing with Dragons'.

STATEMENT REGARDING PRIOR DISCLOSURES UNDER 37 CFR 1.77(B)(6)

*Hosta* 'Dancing with Dragons' was first introduced by the inventor as a non-enabling description through the International Cultivar Registration Authority registration in early 2019. No plants of *Hosta* 'Dancing with Dragons' have been sold, in this country or anywhere in the world, nor has any disclosure of the new plant been made, more than one year prior the filing date of this application.

BACKGROUND AND ORIGIN OF THE PLANT

The present invention relates to a new and distinct *hosta* plant, *Hosta* 'Dancing with Dragons' hereinafter also referred to as the new plant or by the cultivar name, 'Dancing with Dragons'. *Hosta* 'Dancing with Dragons' was a cross by the inventor between two non-patented, unreleased, proprietary hybrids on Jul. 26, 2012 at a wholesale perennial nursery in Zeeland, Mich., USA. The female parent was identified as H10-132-1 and the male parent was identified as H10-366-1. The new plant was assigned the breeder code 12-132-4 and passed the initial evaluation in the summer of 2014. It has been asexually propagated by division at the same nursery since 2017 and also by careful shoot tip plant tissue culture with the resultant asexually propagated plants having retained all the same traits as the original plant. *Hosta* 'Dancing with Dragons' is stable and reproduces true to type in successive generations of asexual reproduction.

There are nearly 6,000 registered and unregistered *hostas* with The American *Hosta* Society, which is the International Cultivar Registration Authority for the genus *Hosta*, and a similar or larger number of unregistered cultivars. Several of these have blue-green leaf blades with ruffled margins. The most similar *hosta* cultivars known to the applicant are the female parent, H10-132-1; the male parent, H10-366-1; 'Diamond Lake' U.S. Plant Pat. No. 30,769; 'Joy Ride' (not patented); 'Neptune' U.S. Plant Pat. No. 19,674 and 'Waterslide' U.S. Plant Pat. No. 30,303. The female parent has is smaller in habit with smaller foliage. The male parent has broader foliage with more ruffles and forms a larger clump. Both parents have glaucous blue foliage. 'Diamond Lake' has much larger habit and broader foliage than the new plant, and also has more rugose leaf surface. 'Joy Ride' is larger in habit with a wider longer leaf blade and has less glaucous covering over the leaf blade. 'Neptune' is larger in habit and has leaves that are broader and longer. 'Waterslide' is smaller in habit, with less glaucous leaf blades, and the leaf blades are also more folded than the flatter leaves of the new plant. 'Fulda' (not patented) has a smaller habit, has a smaller, narrower leaf without the sinuate margin. 'Medusa' (not patented) has a smaller habit with narrower shiny leaves without glaucous surfaces that are variegated with a near white center and the flowers are deep purple.

Other *Hosta* cultivars may have medium-sized leaf blades with heavily glaucous leaves bases and stiff, thick leaf substance or other individual traits similar to 'Dancing with Dragons' but the new plant differs from the above listed cultivars and all other *hostas* known to the applicant, by the combination of the following traits.

1. Leaves are medium-sized, ovate, with narrowly acute apices and cordate base;
2. Arching leaves have a moderately wavy margin.
3. Strongly glaucous blue-green surfaces that hold all season.
4. Underside of leaf near-white with strongly glaucous covering.

5. Compact mounded habit and useful in the garden as edging or front border, in containers, as a specimen or en masse.
6. Flowers are white, broadly striped down the center of the tepals with light lavender and densely arranged in verticils and individually above foliage.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings shows the new plant in a trial garden at a nursery in Zeeland, Mich. with supplement fertilizer and water as needed.

DETAILED BOTANICAL DESCRIPTION

Figure 1:
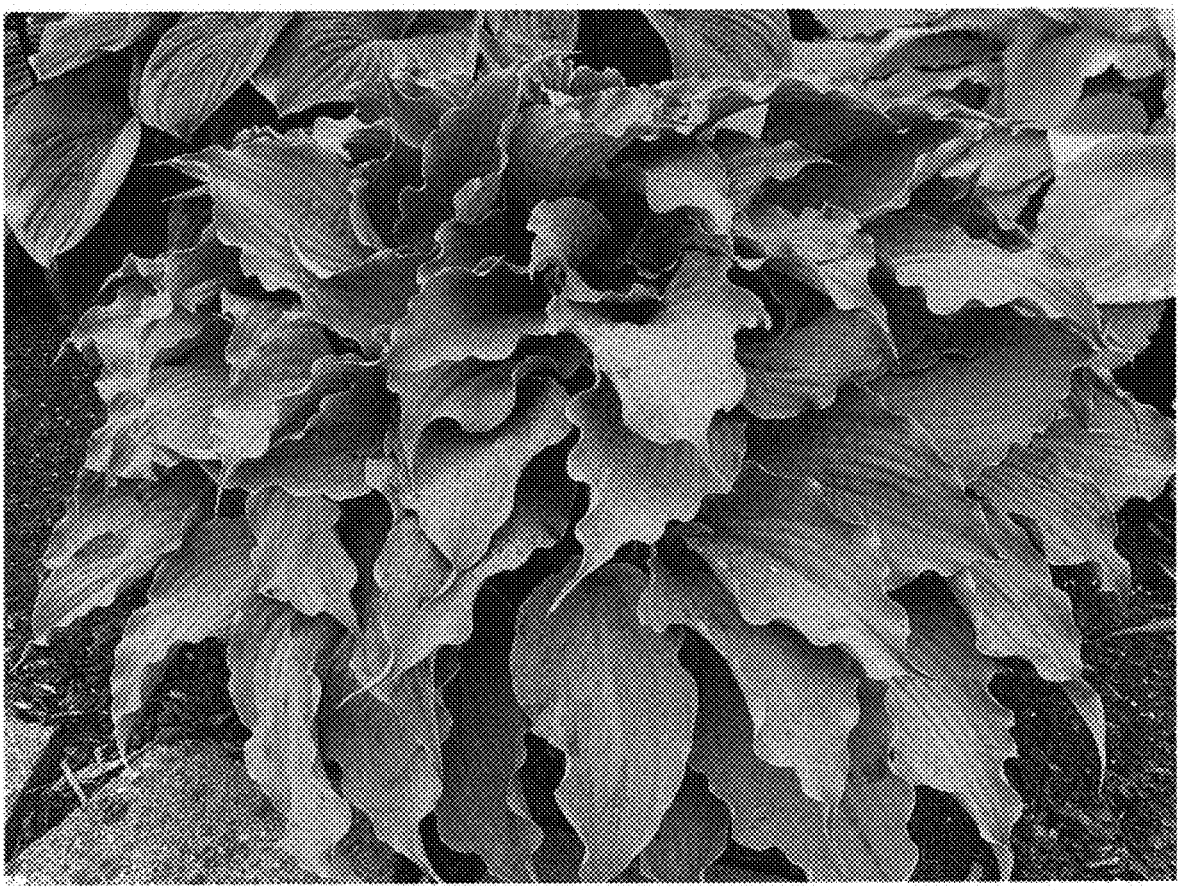
FIG. 1 shows the landscape habit of a six-year-old plant just before flowering.
Figure 2:
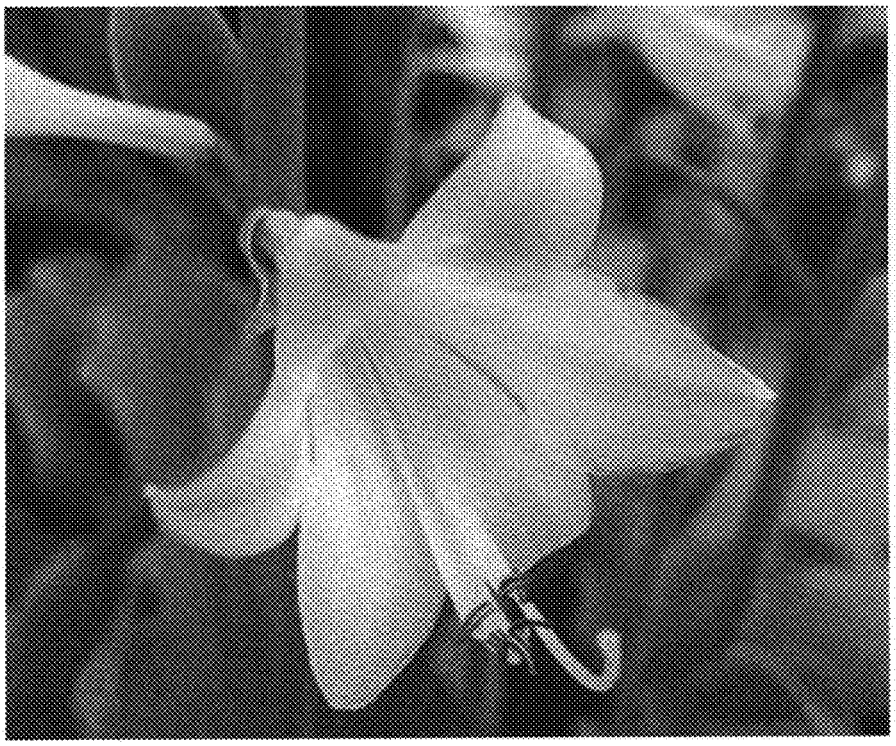
FIG. 2 shows a close-up of the flowers and buds on a six-year-old plant.
Figure 3:
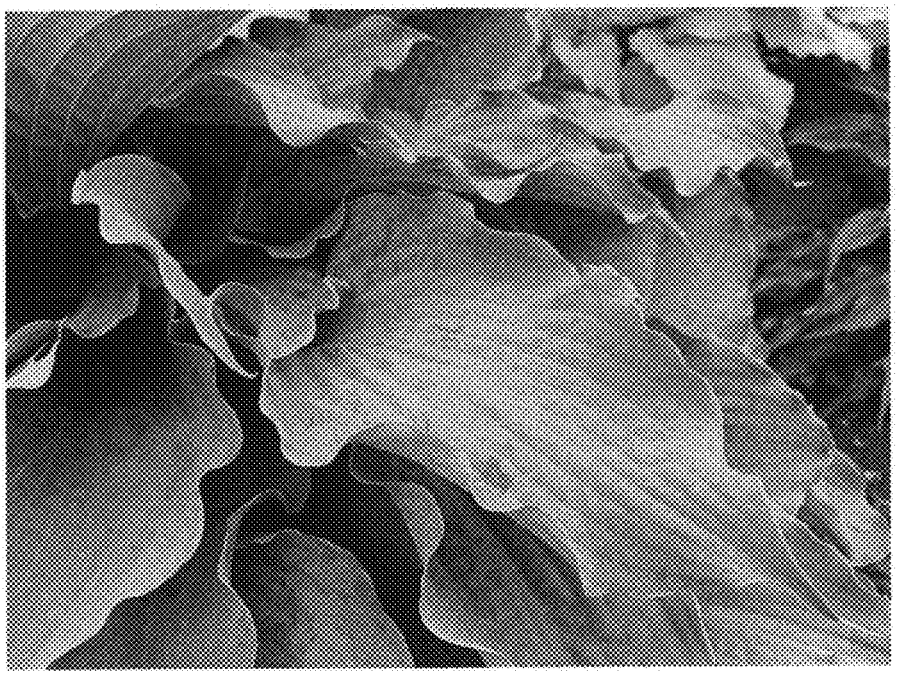
FIG. 3 shows a close-up of the foliage.

The following descriptions and color references are based on the 2015 edition of The Royal Horticultural Society Colour Chart except where common dictionary terms are used. The new plant, *Hosta* 'Dancing with Dragons', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a six-year-old plant in a shaded trial garden in Zeeland, Mich. with supplemental water and fertilizer.

Botanical classification: *Hosta* x hybrid;

Parentage: Female or seed parent the proprietary hybrid H10-132-1 which comprises 'Medusa', a select unpatented proprietary form of *Hosta venusta* (not patented), 'Neptune' and 'Fulda'; male or pollen parent the proprietary hybrid H10-132-1 which comprises 'Neptune', 'Fulda' and 'Joy Ride';

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a short, compact, mound of arching petioles and leaves and upwardly scapes flowering above foliage;

Plant size: Foliage height about 49.0 cm above soil line to the top of the leaves, about 79.0 cm tall to the top of the flowers and about 110.0 cm wide at the widest point at the soil line;

Foliage description: Glabrous and strongly glaucous both adaxial and abaxial; ovate; narrowly acute apex, cordate base; margin entire, moderately sinuate; flexible but stiff; smooth, without blistering, dimpling or bulging;

Leaf blade size: To about 25.5 cm long and 14.0 cm wide; average about 23.0 cm long and 6.2 cm wide; moderately glaucous adaxial and heavily glaucous abaxial;

Leaf blade color: Early season and expanding adaxial blend nearest RHS 189B and RHS N138D, abaxial blend between RHS 188C and RHS 122B; mid-season and later adaxial blend between RHS 189B, RHS 122B and RHS N138D, abaxial nearest blend between RHS 188C and RHS 122B; when glaucous bloom is rubbed or melted off adaxial nearest RHS 146A, abaxial RHS 147B;

Petiole: Glabrous and glaucous both adaxial and abaxial; concavo-convex proximally and more flattened distally; stiff; to 29.5 cm long and 15.0 mm wide at base, average about 28.0 cm long and 14.0 mm wide;

Petiole color: Adaxial and abaxial between RHS 146C and RHS 189B;

Veins: Ten to twelve pairs and midrib; parallel; slightly costate on abaxial side;

Veins color: Aadaxial nearest and RHS 160C; abaxial veins nearest RHS 188C;

Flower description:

Buds one to two days prior to opening: Clavate with rounded apex and narrow tube base; about 24.0 mm long and 8.0 mm in diameter at widest with base narrowing at about mid-length to about 4.0 mm diameter;

Bud color: Between RHS 85C and RHS 85D;

Flowers: Perfect; campanulate; slightly drooping; to 51.0 mm long to exserted stigma; corolla fused in basal 31.0 mm, free in the distal 18.0 mm, about 49.0 mm long and 22.0 mm wide at tepal apices, (distal flowers smaller); corolla tube portion 8.5 mm long and 4.5 mm fused corolla joints vitreous; persists for a normal period, usually one day on plant; lower flowers tightly arranged in verticil near middle and individually separated above and below;

Flowering period: Scapes remain effective with flowers beginning mid-July for about four weeks; with about 75 flowers per scape; distinctly second; no detectable fragrance;

Inflorescence: About 25.0 cm long and 10.0 cm wide;

Tepal: Two nearly identical sets of three, glabrous; entire margins;

*Inner set*.—Fused in basal 31.0 mm; clavate with broadly acute apex; each approximately 49.0 mm long and 14.0 mm wide slightly above fusion point.

*Inner set color*.—Vitreous along margin; adaxial between RHS 85C and RHS 85D in apical 6.0 mm and along 19 mm of central axis, white RHS NN155D proximally and along distal margin; abaxial between RHS 85D and RHS 85C distally along margin and in proximally along midrib of corolla tube.

*Outer set*.—Fused in basal 31.0 mm; clavate with broadly acute apex; each approximately 49.0 mm long and 12.0 mm wide slightly above fusion point.

*Outer set color*.—Not vitreous along margin; adaxial between RHS 85C and RHS 85D in apical, and along 26 mm of central axis, white RHS NN155D proximally and extending distally along margin; abaxial between RHS 85C and RHS 85D distally and along midrib on entire corolla.

Gynoecium: Single; 62.0 mm long; superior;

*Style*.—Cylindrical; about 54.0 mm long, 0.8 mm diameter; curved upward slightly in distal 10.0 mm; color nearest RHS NN155A.

*Stigma*.—Puberulent; tri-lobed; about 1.5 mm across and 1.0 mm tall; color nearest RHS 8C.

*Ovary*.—Ellipsoidal; superior; apex acute; base truncate; to about 7.0 mm long and 3.5 mm diameter in middle; color nearest RHS 145A.

Androecium: Six; to about 55.0 mm long;

*Filaments*.—Six, approximately 54.0 mm long and 0.8 mm in diameter; curved upward to nearly 90 degrees in the apical 10.0 mm; color nearest RHS NN155B.

*Anthers*.—Ellipsoidal with rounded ends; dorsifixed, longitudinally dehiscent; about 4.0 mm long, 1.5 mm wide; color nearest RHS 15B.

*Pollen*.—Spherical; less than 0.1 mm long; color between RHS 10B and RHS 10C.

Flower fragrance: None observed;

Peduncle: Cylindrical, becoming slightly fluted distally; usually one per mature division; 24 per plant; glaucous, glabrous; nearly vertical to slightly outwardly; to about 83.5 cm tall, and about 6.0 mm in diameter at base, average about 74 cm tall and 5.0 mm diameter at base;

Peduncle color: Proximal portion below leaves nearest RHS 190A and distal portion between RHS 188B and RHS 189B;

Pedicel: Variable in length; terete; glabrous; glaucous; about 5.0 mm to 15.0 mm long and 1.5 mm diameter; outwardly to slightly drooping;

Pedicel color: Variable; dorsally nearest RHS 145A, ventrally nearest RHS 193A distally and RHS 155B proximally with distal most 1.0 mm RHS 85B; nearest RHS 194C;

Floral bracts: Each flower normally subtended by a single bract; lanceolate; narrowly acute apex and truncate base; entire margin; glabrous matte surface abaxial and adaxial; decreasing in size distally; average about 15.0 cm long 3.0 mm wide; drying and dehiscing before flowers open;

Bract color: Adaxial and abaxial nearest a blend of RHS 189B and RHS N138D;

Fruit: Tri-valved dehiscent capsule; ellipsoidal to cylindrical with apiculate apex and attenuate base; about 24.0 mm long and 6.5 mm diameter;

Fruit color: Between RHS N138B and RHS 147B;

Seed: Typically about 27 per capsule; endospermic; flattened-ellipsoidal wing surrounding embryo at one end of ellipse; to about 7.0 mm long, 3.0 mm wide and 1.2 mm thick at embryo;

Disease resistance: The thick glaucous leaves provide some resistance to slug feeding. Other resistance to pests (including: *Odocoileus virginianus* and *Oryctotagus cuniculus*) and diseases common to *hostas* is equal that typical of other cultivars. The plant grows best and shows best coloration with plenty of moisture, adequate drainage and light shade, but is able to tolerate some drought when mature. Hardiness at least from USDA zone 3 through 8, and other disease resistance is typical of that of other *hostas*.

It is claimed:

1. A new and distinct *Hosta* plant cultivar named *Hosta* 'Dancing with Dragons' as herein described and illustrated.

* * * * *